United States Patent
Li et al.

(10) Patent No.: US 9,447,126 B2
(45) Date of Patent: Sep. 20, 2016

(54) METHODS AND SYSTEMS FOR CAMPTOTHECIN ANALOG SYNTHESIS

(71) Applicant: ARNO THERAPEUTICS, Flemington, NJ (US)

(72) Inventors: Bin-Feng Li, Suzhou Industrial Park (CN); Ke Yuan, Tianjin (CN)

(73) Assignee: ARNO THERAPEUTICS, INC., Flemington, NJ (US)

( * ) Notice: Subject to any disclaimer, the term of this patent is extended or adjusted under 35 U.S.C. 154(b) by 0 days.

(21) Appl. No.: 14/918,263

(22) Filed: Oct. 20, 2015

(65) Prior Publication Data

US 2016/0115183 A1    Apr. 28, 2016

Related U.S. Application Data

(60) Provisional application No. 62/067,065, filed on Oct. 22, 2014.

(51) Int. Cl.
*C07F 7/02* (2006.01)
*C07D 491/147* (2006.01)
*C07F 7/18* (2006.01)

(52) U.S. Cl.
CPC .................. *C07F 7/1892* (2013.01)

(58) Field of Classification Search
USPC ...................................... 546/14, 89
See application file for complete search history.

(56) References Cited

U.S. PATENT DOCUMENTS

| | | | |
|---|---|---|---|
| 6,150,343 A * | 11/2000 | Curran | A61K 31/437 514/63 |
| 6,177,568 B1 | 1/2001 | Jew et al. | |
| 6,372,906 B1 | 4/2002 | Curran et al. | |
| 2004/0106830 A1 | 6/2004 | Ogawa et al. | |
| 2008/0103309 A1 | 5/2008 | Laitinen | |

OTHER PUBLICATIONS

International Search Report of PCT Application No. PCT/US2015/056499 mailed Jan. 5, 2016.

* cited by examiner

*Primary Examiner* — Charanjit Aulakh
(74) *Attorney, Agent, or Firm* — VLP Law Group LLP; Jeremy A. Cubert (57) ABSTRACT

Methods and systems for making camptothecin analogs and intermediates are provided. Aspects include safer and lower cost methodologies for making camptothecin analogs and intermediates from synthetic materials. In another aspect, the methods and systems can achieve a yield of the camptothecin analogs greater than about 0.4%.

1 Claim, 13 Drawing Sheets

METHODS AND SYSTEMS FOR CAMPTOTHECIN ANALOG SYNTHESIS

PRIORITY CLAIM

This application claims priority to U.S. Provisional Patent Application Ser. No. 62/067,065, filed Oct. 22, 2014. The above referenced application is incorporated herein by reference as if restated in full.

All references cited herein, including but not limited to patents and patent applications, are incorporated by reference in their entirety.

BACKGROUND

Camptothecin is a topoisomerase I inhibitor originally isolated from the bark and stem of Camptothecaacuminata (Camptotheca, Happy tree), a tree native to China.

Camptothecin analogs having anti-cancer and anti-tumor properties are described in U.S. Pat. No. 6,136,978, hereby incorporated by reference in its entirety. In one aspect, these camptothecin analogs have the following general structure (Formula I) described in U.S. Pat. No. 6,136,978 ("'978 patent"):

where $R^1$-$R^{11}$ are defined as in the '978 (e.g., col. 3, line 35—col. 4, line 65).

Of particular interest is a camptothecin analog known as AR-67 or DB-67 ((20S)-10-hydroxy-7-trimethylsilylcamptothecin)) (Formula II) having the structure shown below:

Topoisomerases regulate the winding and unwinding of DNA strands. Camptothecins are DNA topoisomerase I inhibitors which stabilize single-strand breaks in DNA leading to apoptosis and cell death. A general scheme for synthesizing the compound of Formula I is provided in FIG. 1 of the '978 patent.

A known general scheme for synthesizing AR-67 (the compound of Formula II is shown below:

In this synthesis method, the starting material, 10-hydroxycamptothecin, is a natural product obtained from Camptothecaacuminate that requires special handling due to toxicity. In addition, the cost of this starting material is high. Thus, use of known synthesis methods for making the Camptothecin analogs of Formula I and, in particular, AR-67, may be cost prohibitive due the cost of the starting materials and special facilities and handling needed for the starting materials and intermediaries.

What is needed is an improved, less costly method for making, forming, or synthesizing the compounds of Formula I, including AR-67, with higher yields, fewer impurities, lower cost, and less risk.

SUMMARY

In one aspect, methods are described herein for synthesis of the compound of Formula I:

Formula I where $R^1$-$R^{11}$ are defined as in the '978 (e.g., col. 3, line 35—col. 4, line 65).

In another aspect, methods are described herein for the synthesis of the compound of Formula II:

Formula II

Figure 1:
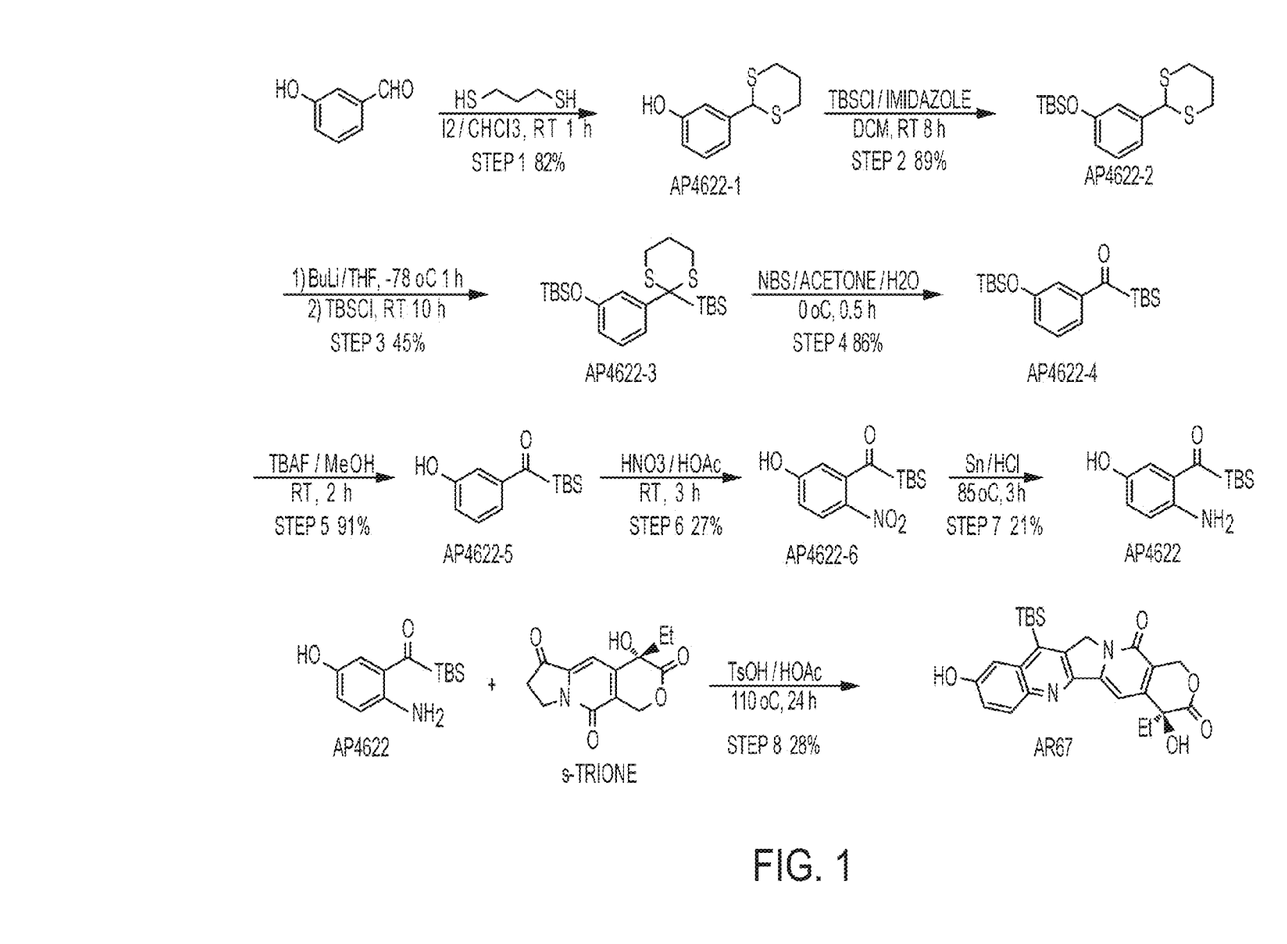
FIG. 1 shows an exemplary eight step synthesis scheme for AR-67.

In yet one aspect, an exemplary method of synthesizing the compounds of Formula I and Formula II is shown in FIG. 1.

In this aspect, synthetic materials can be used as starting materials (e.g., Propane-1,3-dithiol and 3-hydroxybenzaldehyde) resulting in lower risk of toxicity. In another aspect, synthesis methods described herein result in yields of Formula I or Formula II of greater than about 0.4%.

DETAILED DESCRIPTION

Before describing several exemplary aspects described herein, it is to be understood that the invention is not limited to the details of construction or process steps set forth in the following description. The aspects described herein are capable of being practiced or being carried out in various ways. For example, the compound(s) at each step of the exemplary synthesis method can be converted to another compound by a variety of methodologies known to those skilled in the art in addition to the methods described herein (e.g., alternate reagents, temperatures, reaction time, and stirring times).

Aspects described herein provide methods and systems for synthesis of the compounds of Formula I and the synthesis of AR-67 (Formula II). In one aspect, the methods and systems use synthetic and significantly less toxic starting materials than previous methods and systems and result in increased yield with fewer impurities. In another aspect, intermediates in the synthesis of camptothecin analogs are provided.

In one aspect, step 1 of an exemplary synthesis method comprises:

In step 1, Propane-1,3-dithiol (21.64g, 200 mmol) is added dropwise to a solution of iodine (5.08 g, 20 mmol) and 3-hydroxybenzaldehyde (24.42 g, 200 mmol) in $CHCl_3$ (500 mL) at room temperature (RT). The reaction mixture is stirred for 1 hour at RT, then quenched by addition of a solution of $Na_2SO_3$ (5%, 150 mL) and extracted with DCM (250 mL×2).

Figure 2:
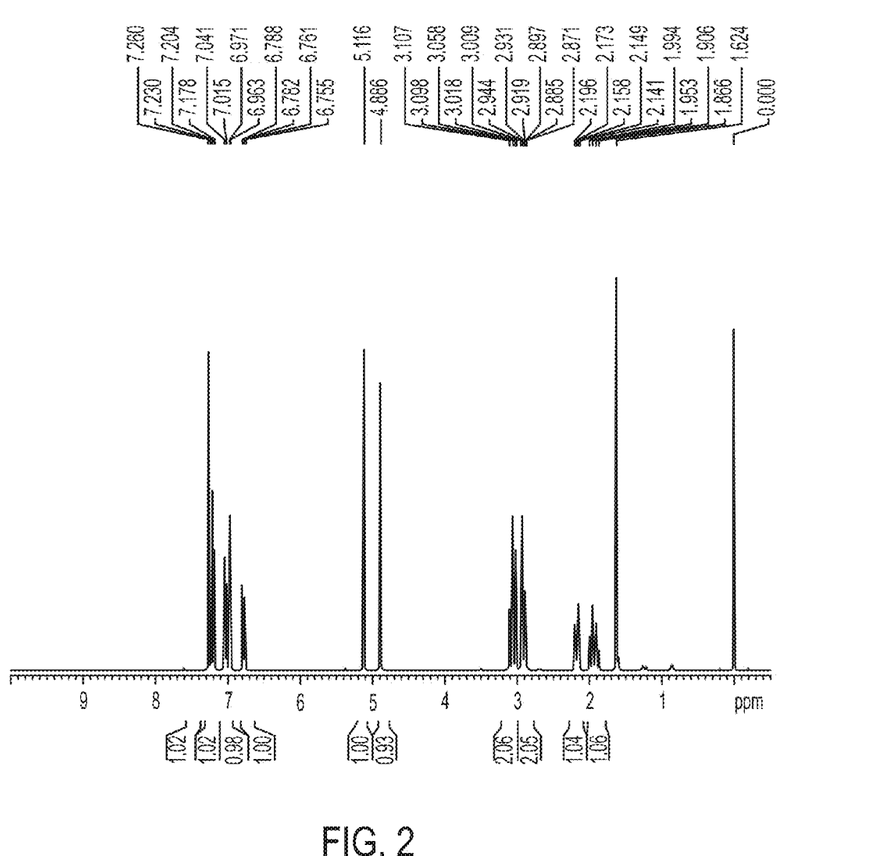
FIG. 2 shows an exemplary NMR spectra for the synthesis of AP4622-1 in step 1 of the synthesis scheme of FIG. 1.

The combined organic layers can be dried over MgSO4, concentrated in vacuo and purified by flash chromatography (EA: Hex=1: 5) to give AP4622-1 as a white powder, 34.82 g, 82% yield. $^1$H NMR (300 MHz, $CDCl_3$) δ 7.20 (t, J=7.8 Hz, 1 H), 7.02 (d, J=7.8 Hz, 1 H), 6.96 (d, J=2.1 Hz, 1 H), 6.77 (dd, J=7.8, 2.1 Hz, 1H), 5.12 (s, 1 H), 4.89 (s, 1 H), 3.02 (m, 2 H), 2.92 (m, 2 H), 2.16 (m, 1 H), 1.95 (m, 1 H) (FIG. 2).

Figure 3:
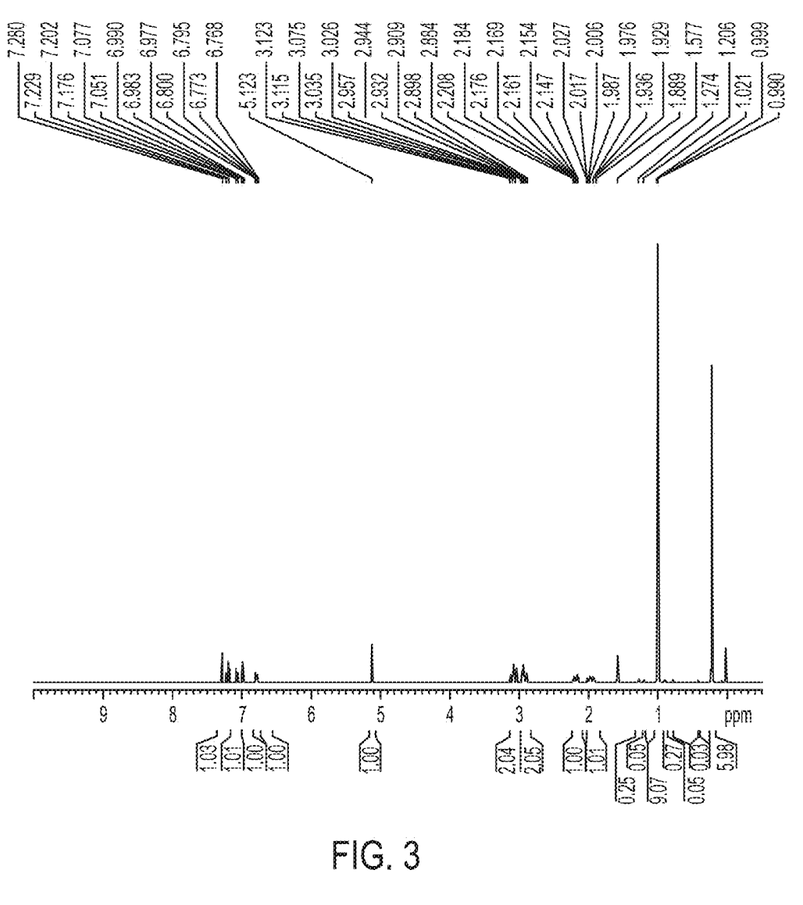
FIG. 3 shows an exemplary NMR spectra for the synthesis of AP4622-2 in step 2 of the synthesis scheme of FIG. 1.

In this aspect, step 2 of an exemplary synthesis method comprises:

In step 2, under argon, a solution of TBSCl (120 mmol, 18.09 g) in DCM (50 mL) is added dropwise to a solution of AP4622-1 (100 mmol, 21.23 g) and imidazole (130 mmol, 8.85 g) in DCM (250 mL) at 0° C. Next, the reaction mixture is stirred overnight at RT, washed with water (200 mL×2), dried over MgSO$_4$ and concentrated in vacuo. The residue can be purified by flash chromatography (EA: Hex=1: 20) to give AP4622-2 as a pale yellow oil, 29.07g, 89% yield. $^1$H NMR (300 MHz, CDCl$_3$) δ 7.20 (t, J =7.8 Hz, 1 H), 7.06 (d, J=7.8 Hz, 1 H), 6.98 (t, J=1.8 Hz, 1 H), 6.77 (dd, J=7.8, 1.8 Hz, 1 H), 5.12 (s, 1 H), 3.07 (m, 2 H), 2.94 (m, 2 H), 2.17 (m, 1 H), 1.98 (m, 1 H), 1.02 (s, 9 H), 0.23 (s, 6 H) (FIG. 3).

Figure 4:
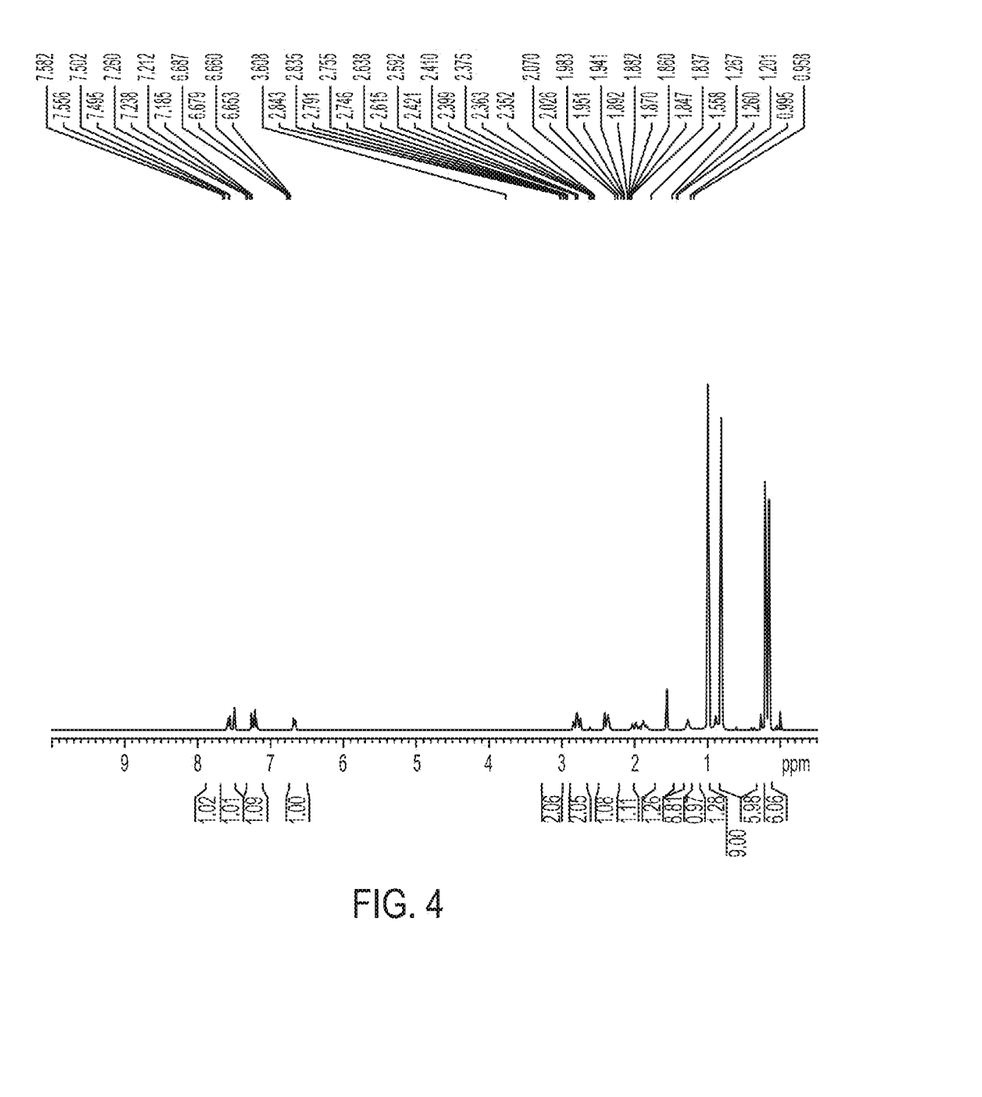
FIG. 4 shows an exemplary NMR spectra for the synthesis of AP4622-3 in step 3 of the synthesis scheme of FIG. 1.

In this aspect, step 3 of an exemplary synthesis method comprises:

In step 3, under argon, n-BuLi (43.6 mL, 2.2 M in hexane, 96mmol) is added dropwise to a solution of AP4622-2 (26.13 g, 80 mmol) in THF (350 mL) at -78 ° C. The resulting mixture can be stirred for additional 1 h at -78° C. followed by addition of TBSCl (16.58 g, 110 mmol) and additional stirring for 10 hours at RT. A saturated solution of NH$_4$Cl (150 mL) can be beadded to quench the reaction. The mixture can be extracted with EA (Ethyl Acetate) (250 mL×2) and the combined organic layers can be dried over MgSO$_4$, concentrated in vacuo, and purified by flash chromatography (EA: Hex=1: 50) to give AP4622-3 as a colorless oil, 15.87 g, 45% yield. $^1$H NMR (300 MHz, CDCl$_3$) δ 7.57 (d, J=7.8 Hz, 1 H), 7.50 (d, J=2.1 Hz, 1 H), 7.21 (t, J=7.8 Hz, 1 H), 6.67 (dd, J=7.8, 2.1 Hz, 1 H), 2.83 (m, 2 H), 2.42 (m, 2 H), 2.07 (m, 1 H), 1.88 (m, 1 H), 1.00 (s, 9 H), 0.83 (s, 9 H), 0.23 (s, 6 H), 0.16 (s, 9 H) (FIG. 4).

Figure 5:
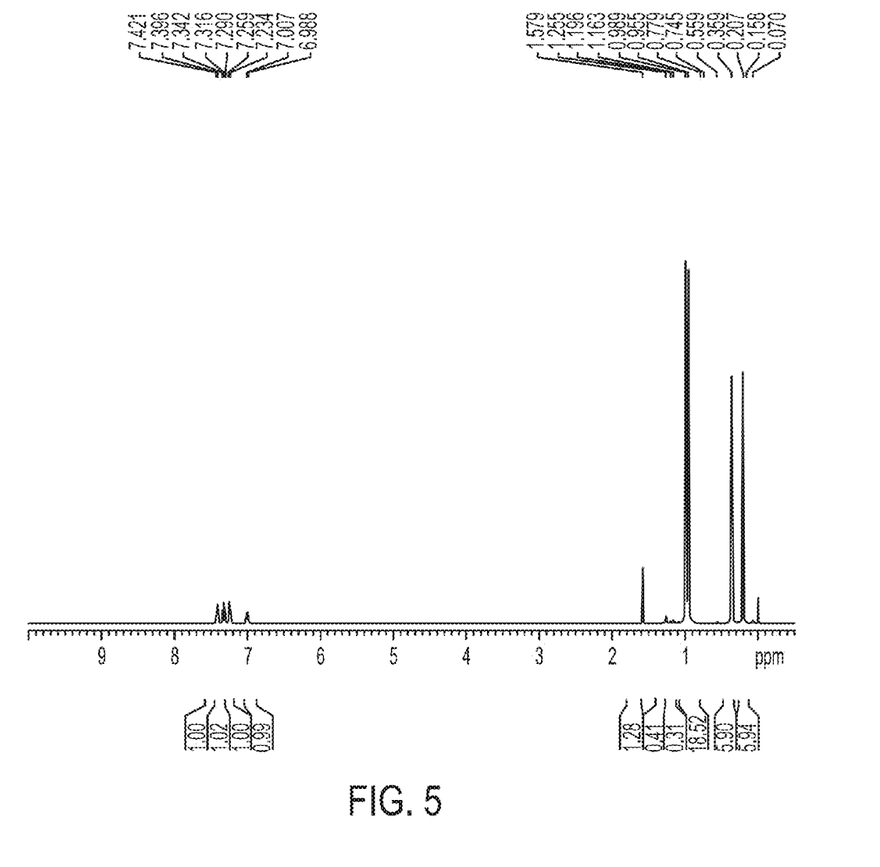
FIG. 5 shows an exemplary NMR spectra for the synthesis of AP4622-4 in step 4 of the synthesis scheme of FIG. 1.

In this aspect, step 4 of an exemplary synthesis method comprises:

In step 4, a solution of AP4622-3 (4.41 g, 10 mmol) in acetone (35 mL is added dropwise to a solution of NBS (8.90 g, 50 mmol) in acetone/water (60 mL/50 mL) at 0 ° C. During the addition, the pH is maintained to neutral by simultaneous addition of Et$_3$N. The resulting mixture is stirred for additional 0.5 h at 0° C. A solution of Na$_2$SO$_3$ (5%, 150 mL) is added to quenched the reaction. The mixture was extracted with EA (100 mL×3). The combined organic layers were dried over MgSO$_4$, concentrated in vacuo and purified by flash chromatography (EA: Hex=1: 100) to give AP4622-4 as a yellow oil, 3.02 g, 86% yield. $^1$H NMR (300 MHz, CDCl$_3$) δ 7.41 (d, J=7.8 Hz, 1 H), 7.32 (t, J=7.8 Hz, 1 H), 7.23 (s, 1 H), 6.99 (d, J=5.7 Hz, 1 H), 0.99 (s, 9 H), 0.96 (s, 9 H), 0.36 (s, 6 H), 0.21 (s, 9 H) (FIG. 5).

Figure 6:
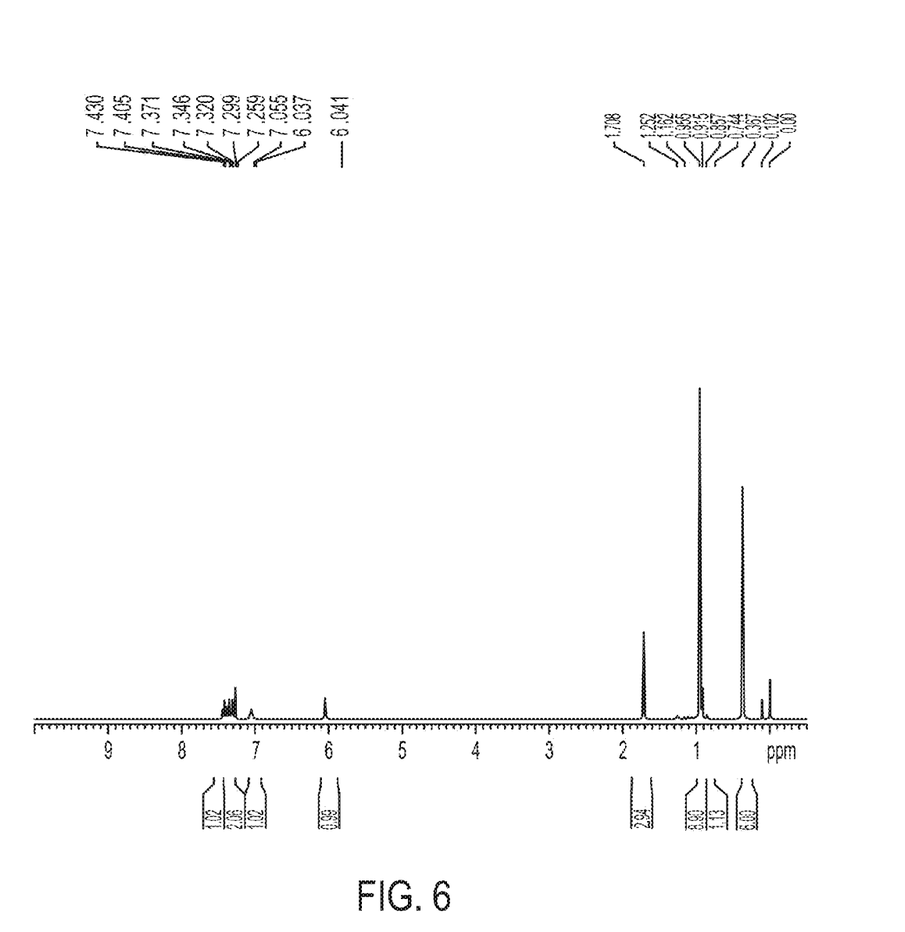
FIG. 6 shows an exemplary NMR spectra for the synthesis of AP4622-5 in step 5 of the synthesis scheme of FIG. 1.

In this aspect, step 5 of the exemplary synthesis method comprises:

In step 5, tetrabutylammonium fluoride trihydrate (3.155 g, 10.0 mmol) is added to a solution of AP4622-4 (1.753 g, 5.0 mmol) in MeOH (20 mL) and the reaction mixture is stirred for 2 hours at RT. The solvent was evaporated in vacuo. The residue is diluted with ethylene acetate (EA) (100 ml), washed with water (50 mL×3), dried over MgSO$_4$, and concentrated in vacuo to provide AP4622-5 as a yellow powder, 1.075 g, 91% yield. $^1$H NMR (300 MHz, CDCl$_3$) δ 7.40 (m, 1 H), 7.32 (m, 2 H), 7.04 (d, J=5.4 Hz, 1 H), 6.04 (s, 1 H), 0.96 (s, 9 H), 0.37 (s, 6 H) (FIG. 6).

Figure 7:
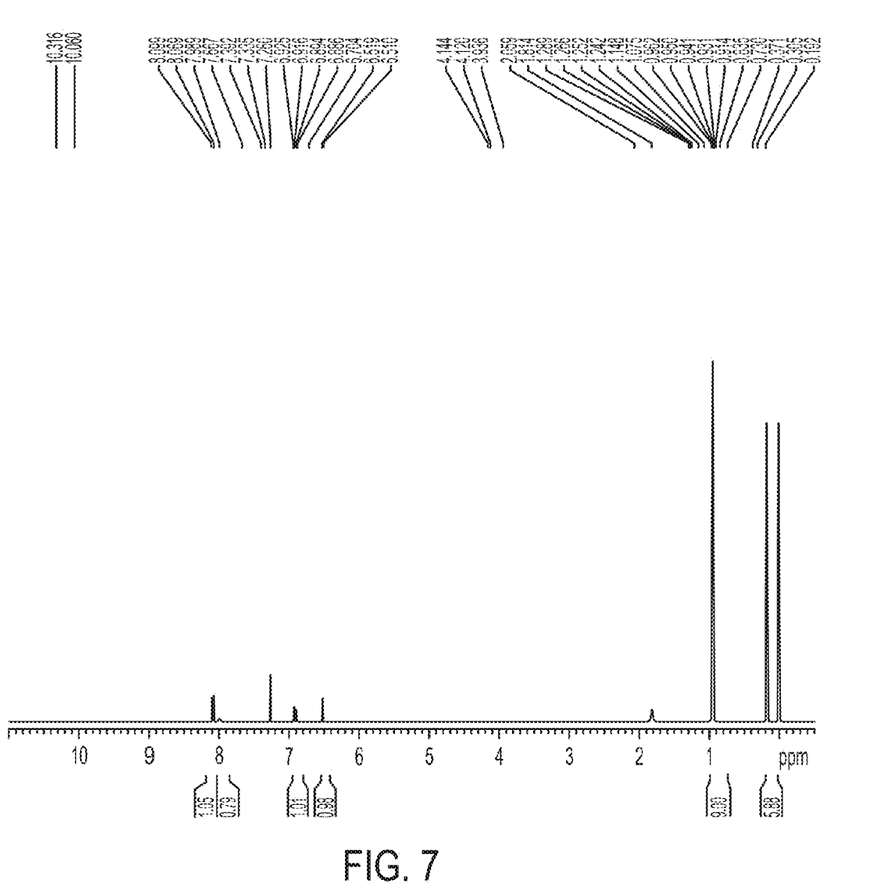
FIG. 7 shows an exemplary NMR spectra for the synthesis of AP4622-6 in step 6 of the synthesis scheme of FIG. 1.

In this aspect, step 6 of the exemplary synthesis method comprises:

In step 6, HNO$_3$ (35%, 1.44 g. 8.0 mmol) is added dropwise to a solution of AP4622-5 (945 mg, 4.0 mmol) in HOAc (10 mL) at 16° C., the reaction mixture is stirred for 3 h at RT, poured into ice water (50 mL), and extracted with ethylene acetate (30 mL×3). The combined organic layers are washed with water (20 mL) and brine (20 mL), dried over MgSO$_4$, concentrated in vacuo, and purified by flash chromatography (EA: Hex =1: 6) to give AP4622-6 as a yellow powder, 304 mg, 27% yield. $^1$H NMR (300 MHz, CDCl$_3$) δ 8.07 (d, J=9.0 Hz, 1 H), 7.99 (s, br, 1 H), 6.90 (dd, J=2.7, 9.0 Hz, 1 H), 6.51 (d, J=2.7 Hz, 1 H), 0.96 (s, 9 H), 0.19 (s, 6 H) (FIG. 7).

Figure 8:
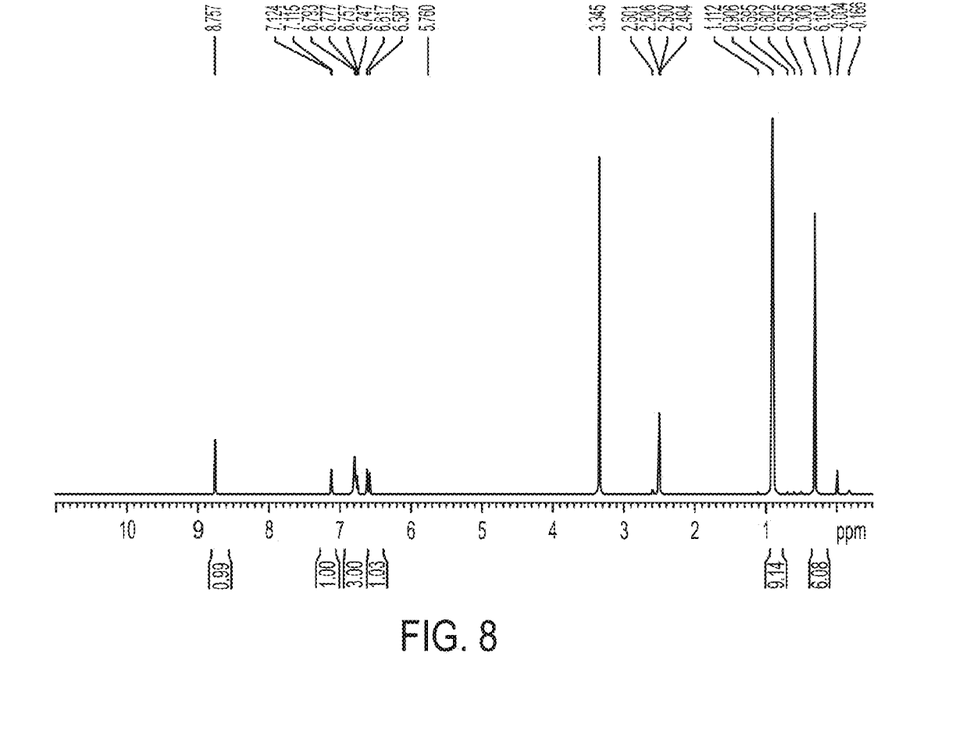
FIG. 8 shows an exemplary NMR spectra for the synthesis of AP4622 in step 7 of the synthesis scheme of FIG. 1.
Figure 9:
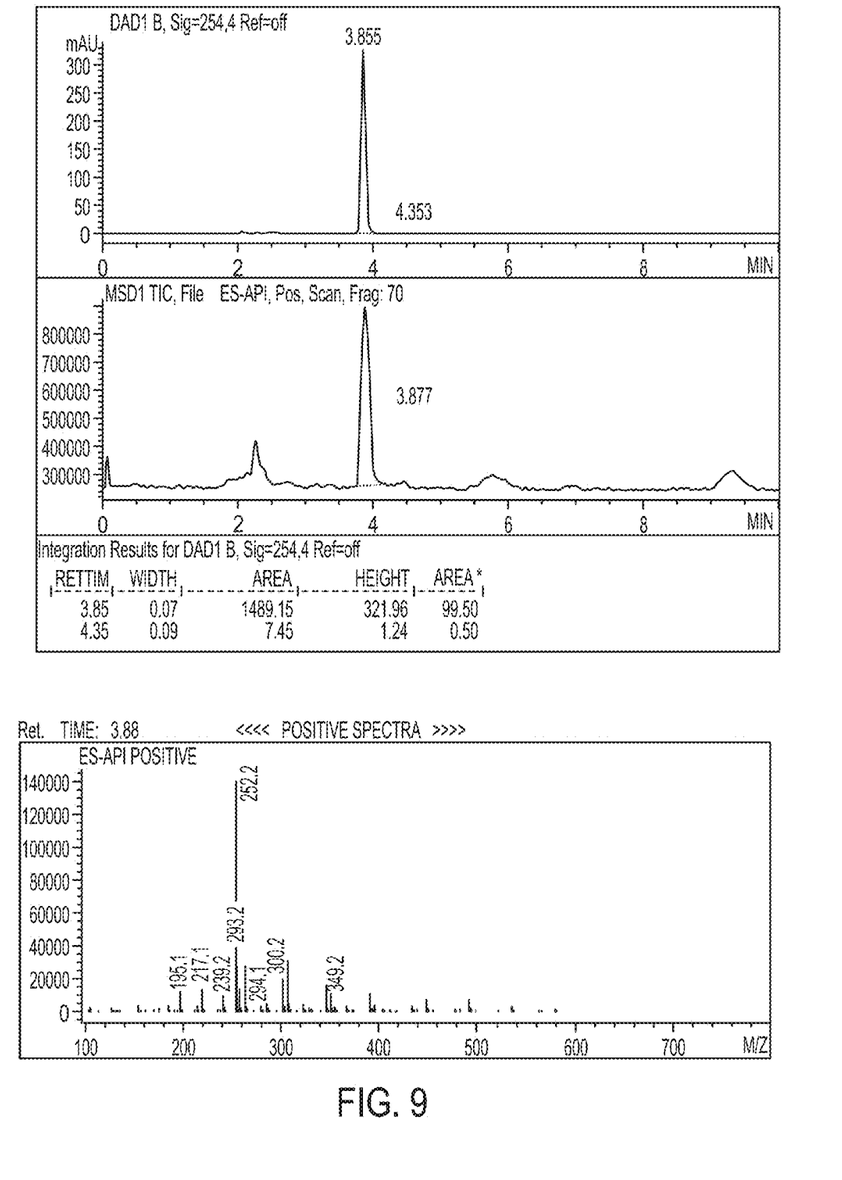
FIG. 9 shows an exemplary LC-MS spectra for the synthesis of AP4622 in Step 7 of the synthesis scheme of FIG. 1.

In this aspect, step 7 of the exemplary synthesis method comprises:

In step 7, tin powder (594 mg, 5.0 mmol) is added to a mixture of AP4622-6 (281 mg, 1.0 mmol) and HCl (3 M, 10 mL) and the reaction mixture is stirred for 3 hours at 85° C. After cooling down, the mixture is extracted with dichloromethane (DCM) (20 mL×3), the combined organic layers are neutralized with Et$_3$N, dried over MgSO$_4$, concentrated in vacuo, and purified by flash chromatography (EA: Hex = 1: 10) to give AP4622-7 as a yellow powder, 53 mg, 21% yield. $^1$H NMR (300 MHz, DMSO-d$_6$) δ 8.76(s, 1 H), 7.12 (d, J=2.7 Hz, 1 H), 6.76 (m, 3 H), 6.60 (d, J=8.7 Hz, 1 H), 0.91 (s, 9 H), 0.31 (s, 6 H) (FIG. 8). LCMS: M+1=252 (FIG. 9).

Figure 10:
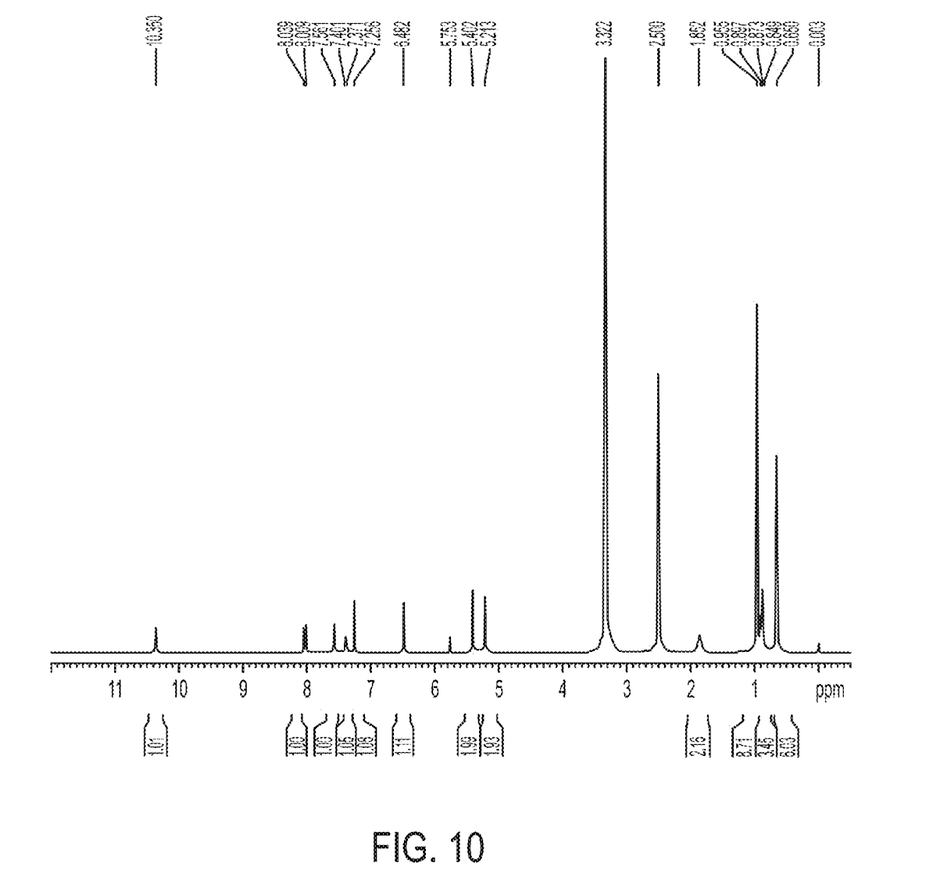
FIG. 10 shows an exemplary NMR spectra for the synthesis of AR-67 in step 8 of the synthesis scheme of FIG. 1.
Figure 11:
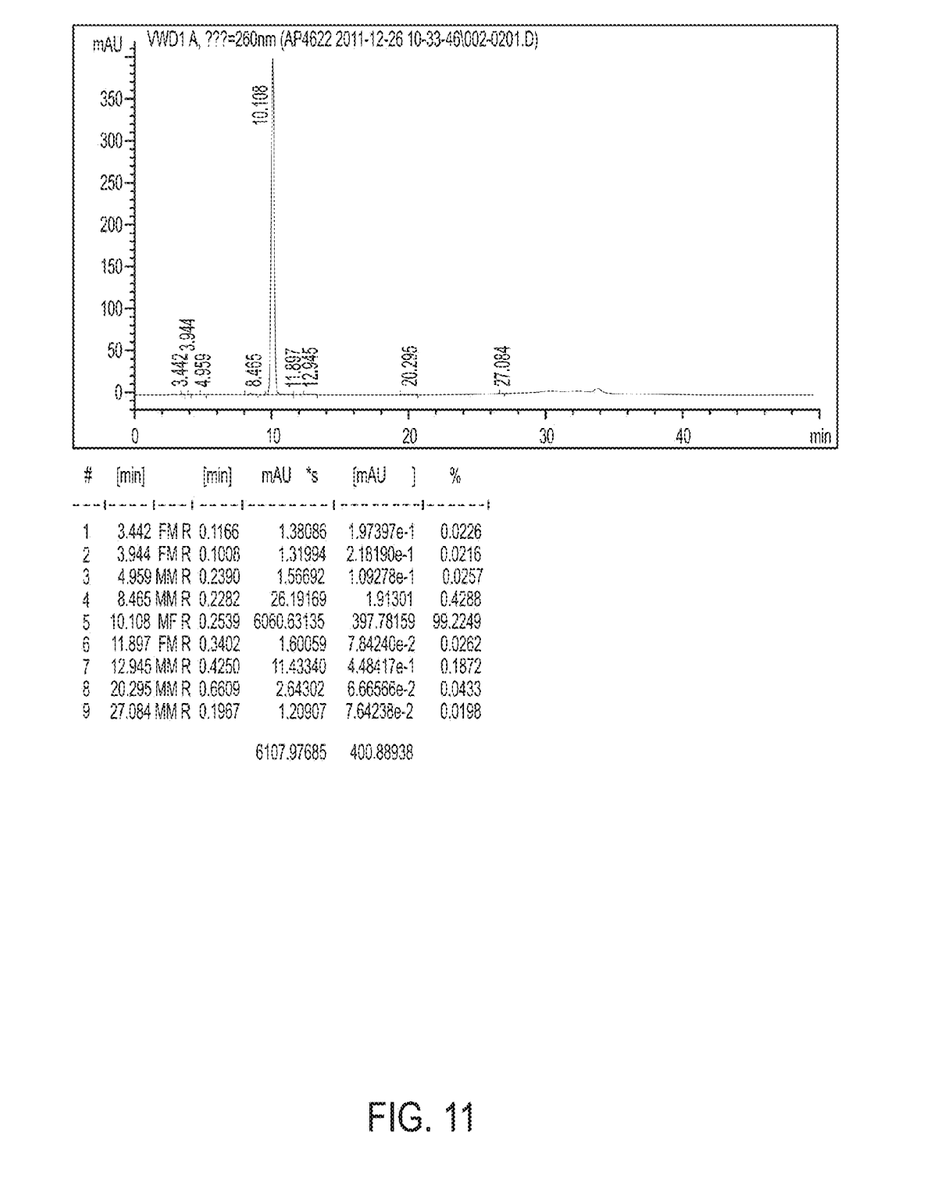
FIG. 11 shows an exemplary HPLC spectra for the synthesis of AR-67 in step 8 of the synthesis scheme of FIG. 1.
Figure 12:
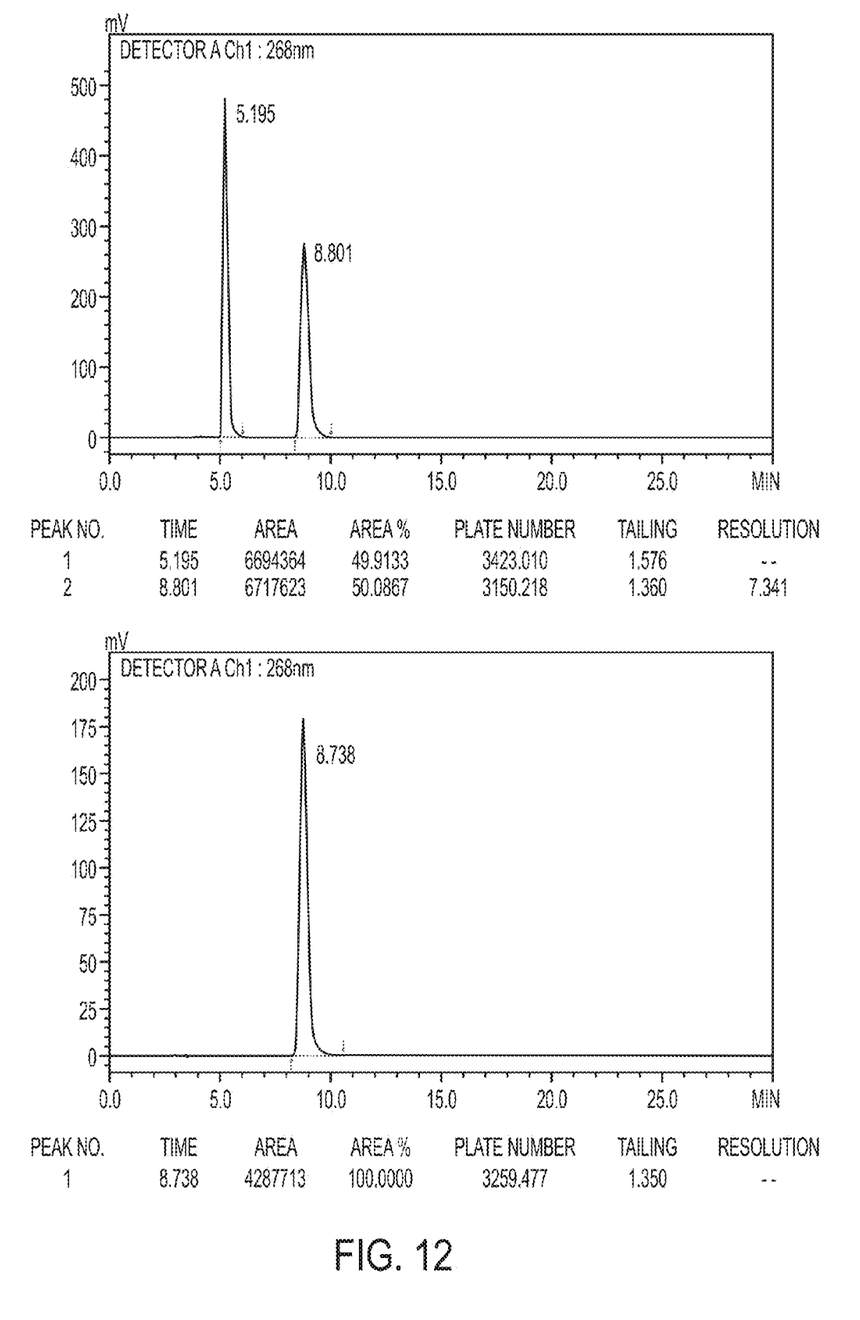
FIG. 12 shows an exemplary chiral HPLC spectra for the synthesis of AR-67 in step 8 of the synthesis scheme of FIG. 1.

In this aspect, step 8 of the exemplary synthesis method comprises:

In step 8, a solution of AP4622 (2.01 g, 8.0 mmol), s-Trione (1.84 g, 7.0 mmol) and TsOH (10 mg, cat) in HOAc (25 mL) is stirred for 24 hours at 110° C. After cooling down, the solvent is removed in vacuo. The residue is purified by flash chromatography (MeOH: DCM=1: 100) to give AR67 as a yellow powder, 950 mg, 28% yield. $^1$H NMR (300 MHz, DMSO-d$_6$) δ 10.35 (s, 1 H), 8.02 (d, J=9.0 Hz, 1 H), 7.56 (s, 1 H), 7.39 (d, J=9.0 Hz, 1 H), 7.26 (s, 1 H), 6.48 (s, 1 H), 5.40 (s, 2 H), 5.21 (s, 2 H), 1.85 (m, 2 H), 0.96 (s, 9 H), 0.87 (t, J=7.2 Hz, 3 H), 0.65 (s, 6 H)(FIG. 10). HPLC Purity: 99.1% (FIG. 11). Chiral HPLC purity: >99% (FIG. 12).

In this aspect, step 9 of the exemplary synthesis method comprises:

-continued

AR67-RAC

Figure 13:
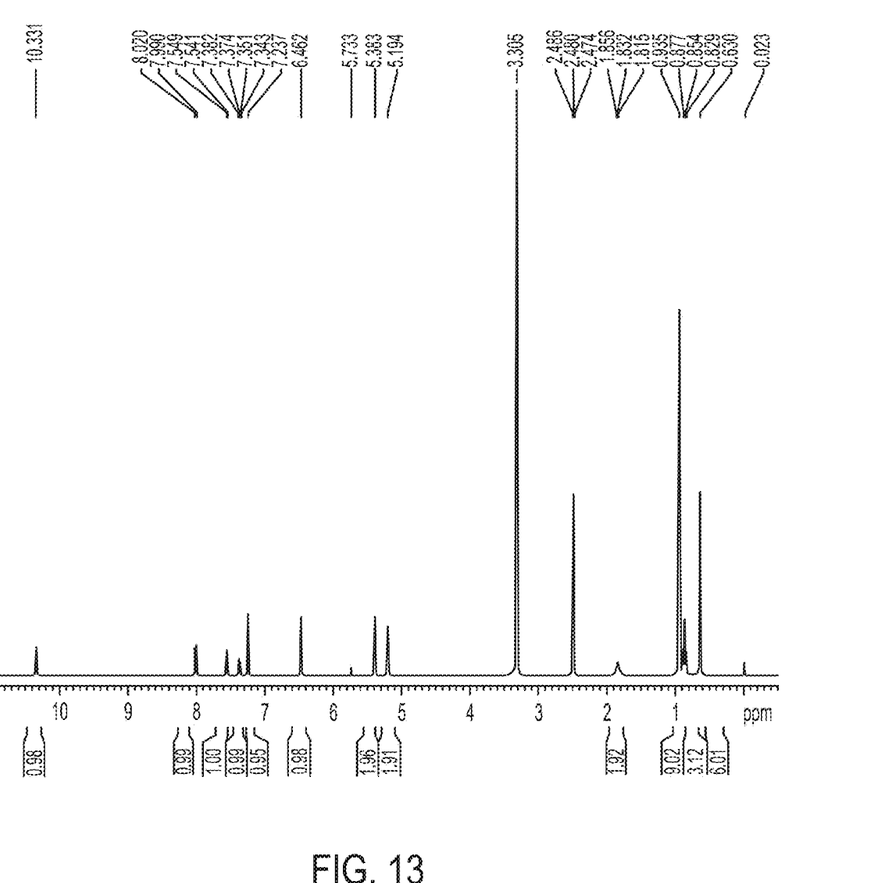
FIG. 13 shows an exemplary NMR spectra for the synthesis of AR-67-RAC in step 9 of the synthesis scheme of FIG. 1.

In this step, a solution of AP4622 (2.01 g, 8.0 mmol), Trione (1.84 g, 7.0 mmol) and TsOH (10 mg, cat) in HOAc (25 mL) is stirred for 24 h at 110° C. After cooling down, the solvent is removed in vacuo. The residue was purified by flash chromatography (MeOH: DCM =1: 100) to give AP4622-RAC (racemic) as a yellow powder, 1.04 g, 31% yield. $^1$H NMR (300 MHz, DMSO-$d_6$) δ 10.35 (s, 1 H), 8.03 (d, J=9.0 Hz, 1 H), 7.56 (d, J =2.4 Hz, 1 H), 7.38 (dd, J=2.4, 9.0 Hz, 1 H), 7.26 (s, 1 H), 6.48 (s, 1 H), 5.40 (s, 2 H), 5.21 (s, 2 H), 1.85 (m, 2 H), 0.96 (s, 9 H), 0.87 (t, J=7.2 Hz, 3 H), 0.65 (s, 6 H) (FIG. 13).

Although the above description refers to particular aspects, it is to be understood that these aspects are merely illustrative. It will be apparent to those skilled in the art that various modifications and variations can be made to the methods described herein. Thus, it is intended that the present description include modifications and variations that are within the scope of the appended claims and their equivalents.

What is claimed is:

1. A method of making the compound AR-67 comprising:
forming AP4622-1 from propane-1,3-dithiol and 3-hydroxybenzaldehyde;
adding a solution of TBSCl to a solution of AP4622-1 and imidazole to form AP4622-2 adding n-BuLi to a solution of AP4622-2 to form a first mixture and adding TBSCl to the mixture to form AP4622-3 adding a solution of AP4622-3 to a solution of NBS to form AP4622-4 adding tetrabutylammonium fluoride trihydrate to a solution of AP4622-4 to form AP4622-5 adding HNO$_3$ to a solution of AP4622-5 to form AP4622-6 adding tin powder to a mixture of AP4622-6 to form AP4622 and
combining AP4622, s-Trione, in the presence of TsOH to form AR-67.

* * * * *